United States Patent [19]

Banka

[11] 4,292,976
[45] Oct. 6, 1981

[54] RIGHT VENTRICULAR INJECTION CATHETER; RIGHT VENTRICULAR ANGIOGRAPHIC METHOD; AND METHOD OF MONITORING SEPTAL WALL MOTION

[76] Inventor: Vidya S. Banka, 237 Stacey Rd., Penn Valley, Narberth, Pa.

[21] Appl. No.: 64,973

[22] Filed: Aug. 8, 1979

[51] Int. Cl.³ .............................................. A61B 6/00
[52] U.S. Cl. .................................. 128/656; 128/658; 128/349 B
[58] Field of Search ............ 128/349 B, 349 BV, 348, 128/344, 350, 10, 654, 651, 658, 657

[56] References Cited

U.S. PATENT DOCUMENTS

| | | | |
|---|---|---|---|
| 2,930,377 | 3/1960 | Cowley | 128/344 |
| 3,411,506 | 11/1968 | Velasco | 128/349 B |
| 3,736,939 | 6/1973 | Taylor | 128/349 B |
| 3,828,767 | 8/1974 | Spiroff | 128/348 |

*Primary Examiner*—Norman Yudkoff
*Attorney, Agent, or Firm*—Benasutti Associates, Ltd.

[57] ABSTRACT

A novel right ventricular injection catheter is disclosed having a balloon tip for disposition in a non-irritable portion of the pulmonary artery, and a distinct injection lumen terminating in a plurality of perforations located 6-8 centimeters from the tip through which materials may be injected into the right ventricle. Using this catheter, it has been found that premature ventricular beats may be avoided, thereby permitting the observation of normal intraventricular septal motion.

7 Claims, 3 Drawing Figures

RIGHT VENTRICULAR INJECTION CATHETER; RIGHT VENTRICULAR ANGIOGRAPHIC METHOD; AND METHOD OF MONITORING SEPTAL WALL MOTION

BACKGROUND OF THE INVENTION

It is often desired to catheterize a patient with one or more catheters which are utilized to inject materials, such as radio-opaque materials, into various portions of the heart to thereby facilitate angiographic observation of various portions of that organ. For example, balloon tipped angiographic catheters (such as "Berman" angiographic catheters) are known having injection orifices for injecting radio-opaque materials, which orifices are located within about 1–2 cm of the tip. In particular, right ventricular angiographic catheterization may advantageously be used for the injection of a contrast agent into the right ventricular chamber for evaluation of contraction patterns of the right ventricle, assessment of tricuspid regurgitation and performance of biventricular angiography for study of interventricular septal motion. Unfortunately, to date, right ventricular angiography has been limited to a considerable extent due to the problems encountered with right ventricular irritability and/or catheter induced arrhythmias which substantially impair the desirability of right ventricular angiography.

SUMMARY OF THE INVENTION

The present invention provides a novel right ventricular catheter and method of using same which avoids ventricular irritability or catheter induced arrhythmias. This catheter and method are particularly adapted for studies of intraventricular septal motion by the simultaneous injection of contrast agents in both the right and left ventricular chambers while observing the left anterior oblique view. In this manner, a new technique providing new ventriculographic physiologic and anatomic observations of cardiac disease is provided.

In accordance with the preferred embodiment of the present invention, the right ventricular angiographic catheter is a double lumen, balloon-tipped catheter which has a blunt closed end. A plurality of holes disposed for angiographic injection are located six to ten centimeters proximal to the tip and communicate with an injection lumen of the catheter. The catheter is advanced from an arm vein (antecubital) and has its tip positioned in the main, right or left pulmonary artery. Once the catheter tip is disposed in the pulmonary artery, the balloon is inflated through an inflation lumen of the catheter to stabilize the catheter tip position and to prevent its inadvertent fall into the right ventricle during pressure injection. Once in this position, the holes of the catheter are located within the right ventricle. Since the tip of the catheter remains in the pulmonary artery, which is a nonirritable area, the contrast medium can be injected into the right ventricle without any irritability and a good right ventriculogram may consequently be obtained.

Accordingly, it has been experimentally determined that the presence of a catheter tip within the right ventricle plays at least some role in the induction of such arrhythmias and that the use of such a catheter and method will substantially prevent the induction of such arrhythmias.

A preferred embodiment method of the present invention accordingly comprises the use of the above described right ventricular angiographic catheter for diagnosing congenital or acquired heart disease. An alternate method comprises the use of this catheter to obtain biventricular angiograms for study of interventricular septal wall motion. According to this alternate method, a standard pigtail angiographic catheter is positioned in the left ventricle. The right ventricular angiographic catheter (as described above) is positioned with its tip in the pulmonary artery and injection orifices in the right ventricle. A test injection is performed to ensure that the injection orifices are adequately positioned for filling the right ventricle. Two volume injectors (preferrably viamonte/Hobbs) are connected, one each to the left and right ventricular catheters. Injections of contrast agent are made simultaneously at a rate of 12–15 cc per second in the left ventricle and 8–12 cc per second in the right ventricle while observing the left anterior oblique view. Cine is made at 60 frames per second for evaluation of contraction patterns of both right and left ventricular chambers and interventricular septal wall motion. In this manner, the anatomy and function of the intraventricular septum is easily observed, and any observable abnormalities may be diagnosed.

DESCRIPTION OF THE PREFERRED EMBODIMENT

Figure 1:
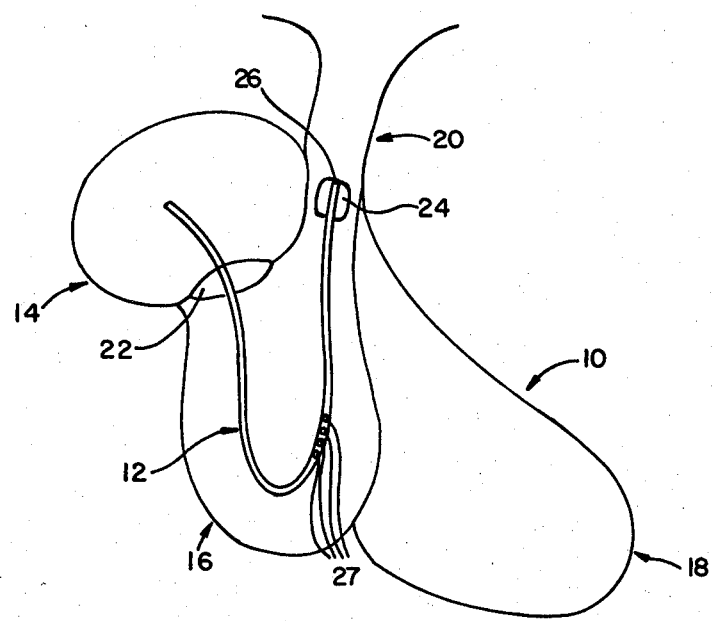
FIG. 1 is a diagrammic view of a foreshortened preferred right ventricular angiographic catheter showing a preferred location of the inflated balloon tip of that catheter disposed within the pulmonary artery of the patient, said catheter having a plurality of injection orifices disposed within the right ventricle of the patient's heart for injection of contrast agents into that right ventricle.

Although specific forms of the invention have been selected for illustration in the drawings, and the following description is drawn in specific terms for the purpose of describing these forms of the invention, this description is not intended to limit the scope of the invention which is defined in the appended claims.

The present invention provides a novel right ventricular angiographic catheter. In the preferred embodiment, this catheter should be from 60 cm to 100 cm in length, with smaller lengths within this range being particularly useful for children. The outer diameter of the preferred embodiment catheter may be from 4 French to 8 French. For an adult population, excellent results have been obtained using a 7 French and 6 French catheter 80 cm in length. The preferred embodiment catheter should have a closed tip, and 2 lumens, a first inner lumen which communicates with the balloon tip, and a second outer lumen which communicates with the injection orifices. These orifices may vary in shape (round, oval, etc.) and be somewhat spaced along the portion of the catheter which is located from 4 to 10 cm proximal of the tip, preferrably 6 to 8 cm from that tip. In the preferred embodiment, these orifices are also positioned for uniform dispersion of contrast agents within the right ventricle, and should not be formed in any manner which would tend to create a rough surface on the outside of the catheter which might irritate the right ventricle.

Referring now to the drawings, and particularly to FIG. 1, a diagrammatic representation of a patient's heart designated generally 10 is illustrated in which the preferred embodiment right angiographic catheter, designated generally 12, is disposed. In this view of the heart, the right atrium designated generally 14, the right ventricle designated generally 16, the left ventricle designated generally 18, and the pulmonary artery designated generally 20, are diagrammatical illustrated. In accordance with the preferred embodiment method of the present invention, the catheter 12 is advanced from an arm vein (antecubital) through the right atrium 14, through the tricuspid valve 22, through the right ventricle 16, and into at least a portion of the pulmonary artery 20. For purposes of simplicity of illustration, however, the right angiographic catheter 12 has been foreshortened in FIG. 1 and is thus not shown extending out of the right atrium towards the arm. As seen in FIG. 1, the balloon tip 24 of the right ventricular catheter 12 has been inflated within the main pulmonary artery. If desired, the catheter may be further advanced into the right or left pulmonary artery prior to inflation of the balloon tip. The preferred embodiment balloon used on this catheter may be of any size and type known to the art, as for example, such as are used for coronary dilation techniques, or, with Swan-Ganz type catheters. As shown in FIG. 1, a plurality of appertures orifices 27 are defined through the outer surface of the right ventricle catheter 12, which appertures permit the injection of contrasting agents into the right ventricle 16. In the preferred embodiment, these appertures are 4 to 10 cm, preferrably 6 to 8 cm, from the tip 26 of the catheter, and are disposed radially around the outer surface of the right ventricular catheter in this region. Although less preferable, at the present time it is anticipated that other injections sites along the ventricular catheter may be utilized as long as those injection sites are disposed within the right ventricle and the tip 26 of the catheter continues to be located in the pulmonary artery.

Figure 2:
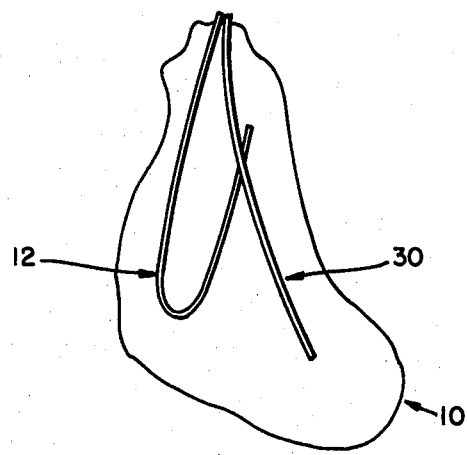
FIG. 2 is a sketch representing an angiographic frame taken from the left anterior oblique view at a stage when the contrast agent has been injected into the right and left ventricular catheters, but has not yet filled their respective ventricles, whereby the location of the catheters within the heart may be readily observed.
Figure 3:
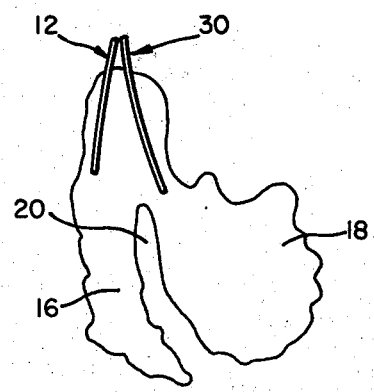
FIG. 3 is a sketch illustrating a subsequent frame of the angiograph of FIG. 2 wherein injection into the right and left ventricle has been completed, thereby permitting the clear observation of the shape of those ventricles and the shape of the septal wall separating those ventricles.

Referring now to the alternate biventricular angiographic method described above, FIG. 2, is a sketch representing a frame of an angiogram taken during the beginning of an injection of contrasting agents simultaneously into right ventricular catheter 12 and left ventricular catheter 30. At this step of the method, the relative positions of the catheters within a faint heart outline 10 is observed. Referring now to FIG. 3, which is a sketch of a subsequent angiographic frame taken following complete injection, the basal portions of left ventricular catheter 30 and right ventricular catheter 12 are still visible, while the tip portions of these catheters are no longer visible by reason of the loss of contrast of those catheters with respect to the contrast agents now filling the right and left ventricular cavities 16 and 18 respectively. It will now be noted, however, that the septal wall 20 and other anatomical and physiologic characteristics of the heart may now be observed on a continuous basis without the incidence of unwanted arrhythmias and/or ventricular irritability. In this manner, particularly when photographically recording the angiograph at 50 to 70 (preferably 60) frames per second, the movement and behavior of the heart, and particularly the interventricular septum, may be observed to diagnose any abnormal conditions, and/or for the purpose of further studying the behavior of the heart. To date, this technique has been used experimentally to produce numerous ventriculargrams. During experimental procedures utilizing this method, no catheter induced arrhythmias have yet been observed.

Numerous changes may be made in the catheter and methods of the present invention without departing from the scope thereof. For example, it is believed that the number of injection orifices may be varied from between 3 to 15, preferably 6 to 12, and that these holes may be disposed in any of a number of patterns within the right ventricular region, as discussed above. It will be further understood that various changes in the details, materials and arrangement of parts which have been herein described and illustrated in order to explain the nature of this invention may be made by those skilled in the art within the principle and scope of the invention as expressed in the following claims. It will further be understood that the "Abstract of the Disclosure" set forth above is intended to provide a non-legal technical statement of the contents of the disclosure in compliance with the Rules of Practice of the U.S. Patent and Trademark Office, and is not intended to limit the scope of the invention described and claimed herein.

I claim:

1. A method of right ventricular angiographic catheterization comprising the steps of:
  (a) providing a catheter of sufficient length for insertion through the right ventricle and into the pulmonary artery of a patient to be catheterized, said catheter having at least one lumen therein, and said lumen communicating with a plurality of injection orifices 4–10 cm from the tip of said catheter, so that the tip of said catheter when inserted into the pulmonary artery positions said orifices in the ventricle;
  (b) inserting said catheter, tip end first, through said right ventricle and into said pulmonary artery to a point where said injection orifices are located within said right ventricle; and
  (c) injecting a contrast medium through said catheter and out said orifices into said right ventricle.

2. A method as claimed in claim 1, further comprising the step of stabilizing said tip of said catheter within said pulmonary artery at least during said injecting step.

3. A method as claimed in claim 2, wherein said catheter has a balloon tip thereon, and wherein said stabilizing step comprises inflating said balloon during at least said injection step.

4. A method of monitoring septal wall motion comprising the steps of:
  (a) providing a catheter of sufficient length for insertion through the right ventricle into the pulmonary artery of a patient to be catheterized, said catheter having at least one lumen, and said lumen communicating with injection orifices 4–10 cm from the tip of said catheter, so that the tip of said catheter when inserted into the pulmonary artery positions said orifices in the ventricle;
  (b) inserting said first catheter through said right ventricle and into said pulmonary artery of said patient to a point where said injection orifices are located within said right ventricle;
(c) providing a second angiographic catheter;
(d) inserting said second catheter into the left ventricle of the patient to be catheterized; and
(e) simultaneously injecting contrast medium into said first and second catheters; whereby said right and left ventricles on either side of said septal wall are filled with contrast medium.

5. A method as claimed in claim 4, further comprising the step of making Cines for evaluating the contraction pattern of both said right and left ventricle chambers and said interventricular septal wall motion.

6. A method as claimed in claim 5, wherein said Cine is made using the left anterior oblique view.

7. A method as claimed in claim 6, wherein said contrast medium is simultaneously injected at a rate of 12-15 cc/second through said second catheter into said left ventricle and 8-12 cc/second through said first catheter into said right ventricle.

* * * * *